United States Patent
Todo et al.

(10) Patent No.: US 10,393,696 B2
(45) Date of Patent: *Aug. 27, 2019

(54) GAS SENSOR

(71) Applicant: DENSO CORPORATION, Kariya, Aichi-pref. (JP)

(72) Inventors: Yusuke Todo, Kariya (JP); Mitsunobu Nakato, Kariya (JP); Hiroaki Yoto, Kariya (JP); Hiroki Ichikawa, Kariya (JP)

(73) Assignee: DENSO CORPORATION, Kariya (JP)

( * ) Notice: Subject to any disclaimer, the term of this patent is extended or adjusted under 35 U.S.C. 154(b) by 68 days.

This patent is subject to a terminal disclaimer.

(21) Appl. No.: 15/650,017

(22) Filed: Jul. 14, 2017

(65) Prior Publication Data

US 2018/0017520 A1    Jan. 18, 2018

(30) Foreign Application Priority Data

Jul. 15, 2016 (JP) .................... 2016-140602

(51) Int. Cl.
| | |
|---|---|
| *G01N 27/417* | (2006.01) |
| *G01N 27/403* | (2006.01) |
| *G01N 27/30* | (2006.01) |
| *C22C 5/04* | (2006.01) |
| *G01N 27/419* | (2006.01) |

(52) U.S. Cl.
CPC ............. *G01N 27/417* (2013.01); *C22C 5/04* (2013.01); *G01N 27/304* (2013.01); *G01N 27/419* (2013.01)

(58) Field of Classification Search
CPC ... G01N 27/417; G01N 27/403; G01N 27/304
See application file for complete search history.

(56) References Cited

U.S. PATENT DOCUMENTS

| | | |
|---|---|---|
| 4,863,583 A | 9/1989 | Kurachi et al. |
| 6,156,175 A | 12/2000 | Kato et al. |
| 6,280,588 B1 | 8/2001 | Kato et al. |

(Continued)

FOREIGN PATENT DOCUMENTS

| | | |
|---|---|---|
| JP | 63-66448 | 3/1988 |
| JP | 2001-201483 | 7/2001 |

(Continued)

*Primary Examiner* — Susan D Leong
(74) *Attorney, Agent, or Firm* — Nixon & Vanderhye P.C.

(57) ABSTRACT

A gas sensor includes a sensor element. The sensor element includes; a solid electrolyte body that has oxygen ion conductivity and includes a first main surface exposed to a gas to be measured and a second main surface exposed to a reference gas; a sensor electrode that is provided on the first main surface and detects a specific gas component in the gas to be measured; and a reference electrode that is provided on the second main surface. The sensor electrode is made of a Pt—Rh alloy that contains 30 mass % to 70 mass % Pt and 70 mass % to 30 mass % Rh, when an overall noble metal component is 100 mass %. A variation amount of the Rh content of the Pt—Rh alloy from an outermost surface to a depth of 350 nm in a thickness direction of the sensor electrode is within a range of up to 10 mass %.

4 Claims, 6 Drawing Sheets

(56) References Cited

U.S. PATENT DOCUMENTS

| | | | |
|---|---|---|---|
| 6,319,377 B1 * | 11/2001 | Hasei | G01N 27/417 |
| | | | 204/425 |
| 2002/0005353 A1 | 1/2002 | Kato et al. | |
| 2002/0162755 A1 | 11/2002 | Kato et al. | |
| 2004/0000479 A1 * | 1/2004 | Katafuchi | G01N 27/419 |
| | | | 204/424 |
| 2005/0210657 A1 | 9/2005 | Nakagaki et al. | |
| 2011/0138875 A1 | 6/2011 | Shindo et al. | |
| 2017/0370874 A1 * | 12/2017 | Nakatou | C22C 5/04 |

FOREIGN PATENT DOCUMENTS

| | | |
|---|---|---|
| JP | 2004-245680 | 9/2004 |
| WO | 2016/111345 | 7/2016 |

* cited by examiner

⟨EXAMPLE⟩

FIG.8

GAS SENSOR

CROSS-REFERENCE TO RELATED APPLICATION

This application is based on and claims the benefit of priority from Japanese Patent Application No. 2016-140602, filed Jul. 15, 2016. The entire disclosure of the above application is incorporated herein by reference.

BACKGROUND

Technical Field

The present disclosure relates to a gas sensor that detects a specific gas component in a gas to be measured.

Related Art

A sensor element of a gas sensor detects a specific gas component, such as NOx (nitrogen oxide), in a gas to be measured. For example, the gas to be measured is exhaust gas that is discharged from an internal combustion engine. In the sensor element, a sensor electrode that contains a Pt—Rh (platinum-rhodium) alloy is used. The sensor electrode is provided on a surface of a solid electrolyte body that is exposed to the gas to be measured. The Rh (rhodium) in the Pt—Rh alloy exhibits catalytic activity relative to NOx, but is also prone to oxidation. When the Rh present near the surface of the sensor electrode forms $Rh_2O_3$ (rhodium oxide) during use of the gas sensor, the catalytic activity of the sensor electrode relative to NOx decreases. Detection accuracy of the gas sensor for the specific gas component decreases.

JP-A-2004-245680 discloses that, during the process of manufacturing a gas sensor element, the Rh in the sensor electrode is oxidized and $Rh_2O_3$ is produced. The $Rh_2O_3$ is then reduced to Rh (rhodium metal) by a sensor cell including the sensor electrode being subjected to an energization process.

In JP-A-2004-245680, it is possible to reduce the $Rh_2O_3$ present near the outermost surface of the sensor electrode to Rh as a result of the energization process being performed. However, as a result of keen research by the inventors, it has been found that, even should the energization process be performed, segregation is present in the Rh in the Pt—Rh alloy that is present in a surface region of the sensor electrode. The surface region is a region from the outermost surface of the sensor electrode to a depth of 350 nm. The segregation indicates that the Rh content in the Pt—Rh alloy changes when a depth position from the outermost surface of the sensor electrode changes. In addition, the segregation is expressed by a difference between a maximum Rh content and a minimum Rh content in the Pt—Rh alloy, as a variation amount of the Rh content in the Pt—Rh alloy.

In cases in which the segregation of Rh is present in the surface region of the sensor electrode, in an initial state of use of the gas sensor, the sensitivity of the sensor electrode to NOx and the like, that is, the catalytic activity of the sensor element, is temporarily high. However, in this case, the vicinity of the sensor electrode is held in a stoichiometric state in which oxygen is minimal, during the use of the gas sensor. Consequently, a phenomenon in which the Rh migrates to the outermost surface of the sensor electrode does not easily occur. In addition, because noble metals become more mobile as a result of thermal energy, Pt and Rh, which are substantially equal in terms of migration energy, change to become homogenous.

At this time, the sensitivity of the sensor electrode to NOx and the like, which has temporarily increased in the initial state, changes to become lower. Therefore, the detection accuracy of the gas sensor for NOx and the like varies with time.

Moreover, it has been confirmed that, when the segregation of Rh that is present in the surface region of the sensor electrode exceeds a predetermined range, a change amount of the sensitivity of the sensor element to a specific gas component, that is, an output change amount of the gas sensor exceeds an allowable range.

SUMMARY

It is thus desired to provide a gas sensor that is capable of suppressing the occurrence of variations with time in detection accuracy for a specific gas component.

An exemplary embodiment of the present disclosure provides a gas sensor including a gas sensor element that detects gas concentration. In the gas sensor, the sensor element includes a solid electrolyte body, a sensor electrode, and a reference electrode. The solid electrolyte body has oxygen ion conductivity, and includes a first main surface that is exposed to a gas to be measured and a second main surface that is exposed to a reference gas. The sensor electrode is provided on the first main surface of the solid electrolyte body, and detects a specific gas component in the gas to be measured. The reference electrode is provided on the second main surface of the solid electrolyte body. The sensor electrode is made of a Pt—Rh alloy that contains 30 mass % to 70 mass % Pt and 70 mass % to 30 mass % Rh, when an overall noble metal component is 100 mass %. A variation amount of the Rh content of the Pt—Rh alloy from an outermost surface of the sensor electrode to a depth of 350 nm in a thickness direction of the sensor electrode is within a range of up to 10 mass %.

In the above-described gas sensor, in the sensor electrode of which the noble metal component is the Pt—Rh alloy, segregation of Rh in the Pt—Rh alloy in a surface region from an outermost surface of the sensor electrode to a depth of 350 nm in the thickness direction is lessened. Specifically, the Pt—Rh alloy of the sensor electrode contains 30 mass % to 70 mass % Pt and 70 mass % to 30 mass % Rh. The variation amount of the Rh content of the Pt—Rh alloy from the outermost surface of the sensor electrode to a depth of 350 nm in the thickness direction is within a range of up to 10 mass %.

In addition, even when segregation of Rh is present within the region from the outermost surface of the sensor electrode to a depth of 350 nm in the thickness direction, the segregation falls within the range of the variation amount of up to 10 mass %. Therefore, during use of the gas sensor, changes in the distribution of Pt and Rh in the sensor electrode hardly occur, and the sensitivity of the sensor electrode to the specific gas component does not easily vary with time.

Here, "within a range of up to 10 mass %" refers to the difference between a maximum Rh content and a minimum Rh content of the Pt—Rh alloy in the region from the outermost surface of the sensor electrode to a depth 350 nm being within 10 mass %. In addition, "10 mass %" is prescribed as the variation amount of the Rh content that is allowable for setting a change amount of the sensitivity of the sensor electrode to the specific gas component, that is, an output change amount of the gas sensor to an allowable range.

Thus, in the above-described gas sensor, the occurrence of variations with time in the detection accuracy for the specific gas component can be suppressed.

DESCRIPTION OF THE EMBODIMENTS

A preferred embodiment of the above-described gas sensor will be described with reference to the drawings.

Figure 1:
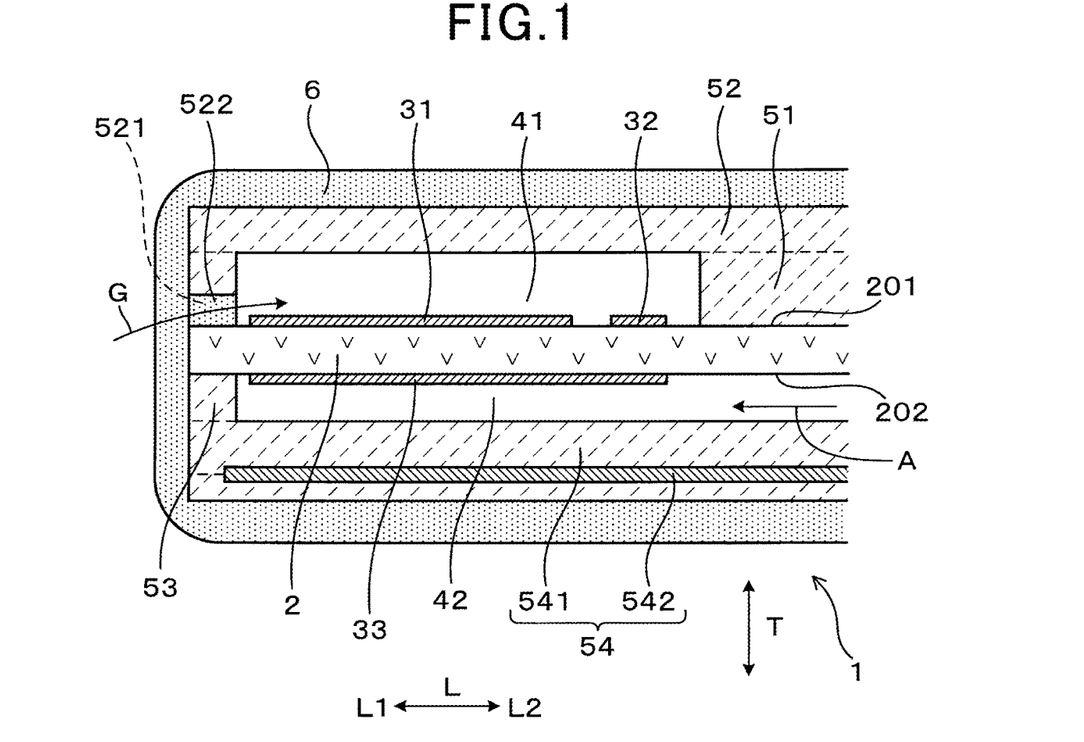
FIG. 1 is a cross-sectional view of a sensor element according to an embodiment.

As shown in FIG. 1, a gas sensor 100 according to the present embodiment takes in exhaust gas that flows through an exhaust system of an internal combustion engine, as a gas to be measured G. The gas sensor 100 then detects the concentration of NOx in the exhaust gas. The NOx serves as a specific gas component. In addition, a reference gas A used in the gas sensor 100 is atmospheric air that has a fixed oxygen concentration.

A sensor element 1 of the gas sensor 100 is configured such that insulators 51 to 53 and a heater 54 are laminated onto a plate-shaped solid electrolyte body 2 that has oxygen ion conductivity. The insulators 51 to 53 are composed of a ceramic. The solid electrolyte body 2 is made of yttria partially stabilized zirconia. Stabilized zirconia or partially stabilized zirconia in which a portion of the zirconia is substituted by a rare earth metal element or an alkali earth metal element can be used in the solid electrolyte body 2. A first main surface 201 of the solid electrolyte body 2 that is exposed to the gas to be measured G is provided with a sensor electrode 32. The sensor electrode 32 detects the specific gas component in the gas to be measured G. A second main surface 202 of the solid electrolyte body 2 that is exposed to the reference gas A is provided with a reference electrode 33. The first main surface 201 and the second main surface 202 compose a pair of the largest surfaces of the solid electrolyte body 2.

The first main surface 201 of the solid electrolyte body 2 is provided with a measured gas chamber 41. The gas to be measured G is introduced into the measured gas chamber 41. The measure gas chamber 41 is formed such as to be surrounded by the first insulator 51 and the plate-shaped second insulator 52. The first insulator 51 serves as a spacer and is laminated onto the first main surface 201 of the solid electrolyte body 2.

As shown in FIG. 1, the second main surface 202 of the solid electrolyte body 2 is provided with a reference gas chamber 42. The reference gas A is introduced into the reference gas chamber 42. The reference gas chamber 42 is formed such as to be surrounded by the third insulator 53 and the plate-shaped heater 54. The third insulator 53 serves as a spacer and is laminated onto the second main surface 202 of the solid electrolyte body 2. The reference gas chamber 42 is formed from a section opposing the reference gas chamber 41 to an end portion of the gas sensor 100 on a proximal end side L2 in a length direction L.

The heater 54 has a ceramic base plate 541 and a heating element 542. The heating element 542 is embedded in the base plate 541 and generates heat by being energized.

A gas introduction opening 521 is formed in a distal end portion of the first insulator 51. The gas introduction opening 521 is used to introduce the gas to be measured G into the measured gas chamber 41. The distal end portion refers to a distal end portion of the elongated sensor element 1 that is exposed to the gas to be measured G. A diffusion resistor 522 is provided in the gas introduction opening 521. The diffusion resistor 522 is used to introduce the gas to be measured G into the measured gas chamber 41 under a predetermined diffusion resistance. The diffusion resistor 522 is made of a porous ceramic body.

The gas to be measured G within the measured gas chamber 41 flows from a distal end side L1 in the length direction L of the sensor element 1 towards the proximal end side L2.

As shown in FIG. 1, a pump electrode 31 is provided on the first main surface 201 of the solid electrolyte body 2, in a position further towards an upstream side of the flow of the gas to be measured G than the position in which the sensor electrode 32 is provided. The pump electrode 31 adjusts the oxygen concentration of the gas to be measured G in the measured gas chamber 41. A noble metal component of the pump electrode 31 is made of a Pt—Au (platinum-gold) alloy. A noble metal component of the reference electrode 33 is made of Pt (platinum).

A single reference electrode 33 according to the present embodiment is provided in a position opposing the pump electrode 31 and the sensor electrode 32, that is, a position at which the pump electrode 31 and the sensor electrode 32 are projected onto the solid electrolyte body 2 in a thickness direction T. The reference electrode 33 can also be provided separately for each of the pump electrode 31 and the sensor electrode 32.

A protective layer 6 is provided in the distal end portion of the sensor element 1. The protective layer 6 captures moisture and substances poisonous to the electrodes 31 and 32, while allowing the gas to be measured G to pass. The protective layer 6 is made of a porous ceramic body.

The gas to be measured G that comes into contact with the distal end portion of the sensor element 1 is introduced into the measured gas chamber 41 after passing through the protective layer 6 and the diffusion resistor 522. In addition, the oxygen concentration of the gas to be measured G in the measured gas chamber 41 is adjusted by a voltage being applied between the pump electrode 31 and the reference electrode 33. Furthermore, the specific gas component in the gas to be measured G after the adjustment of oxygen concentration is decomposed by the sensor electrode 32 and detected based on a current flowing between the sensor electrode 32 and the reference electrode 33.

Figure 2:
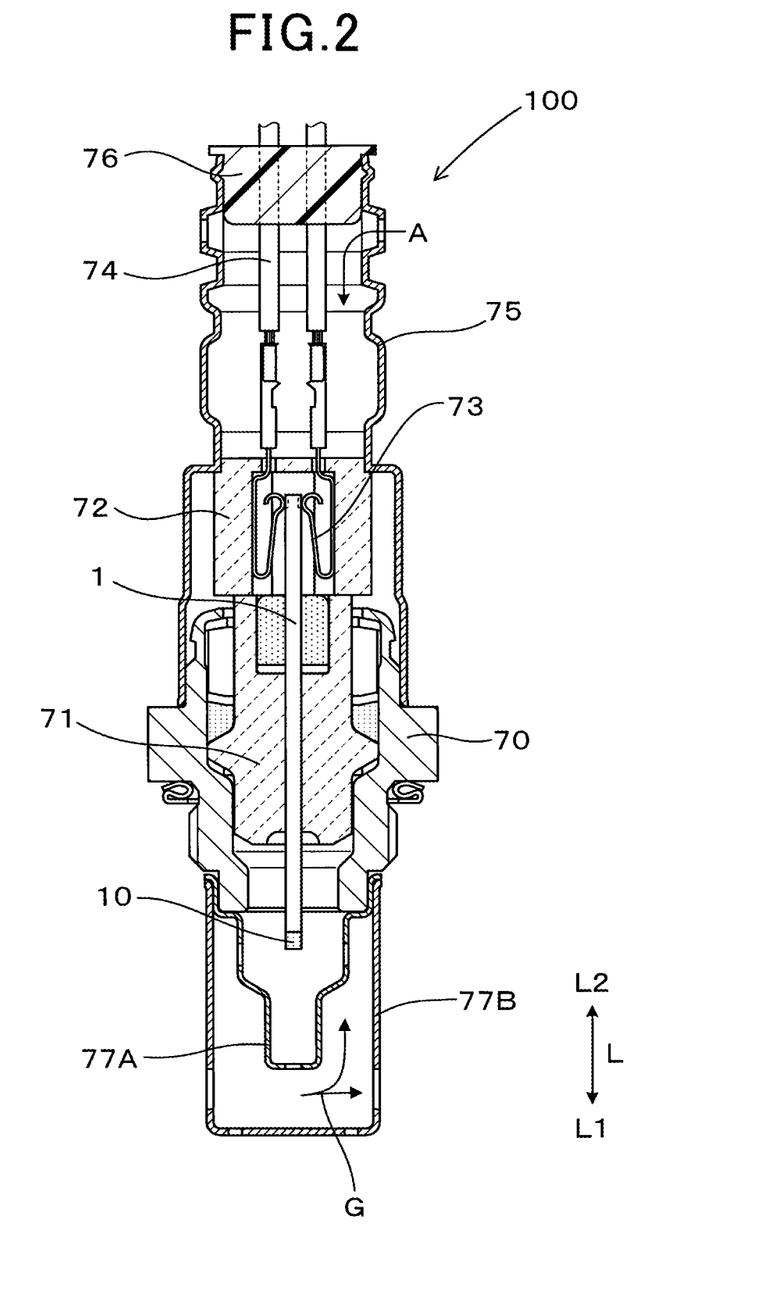
FIG. 2 is a cross-sectional view of a gas sensor according to the embodiment.

As shown in FIG. 2, the gas sensor 100 is formed by the sensor element 1 being assembled to a housing 70, an insulator 71, covers 77A, 77B, and 75, and the like. The sensor element 1 is held within the housing 70 with the insulator 71 therebetween. The sensor element 1 is disposed in an exhaust pipe by the housing 70 that is attached to the exhaust pipe. In addition, the covers 77A and 77B that form a double layer are attached to the housing 70. The covers 77A and 77B cover the distal end portion of the sensor element 1. The sensor element 1 is formed into an elongated shape, and a detecting portion 10 is provided in an end portion of the sensor element 1 on the distal end side L1 in the length direction L. The detecting portion 10 detects the gas to be measured G.

Another insulator 72 is disposed on a proximal end side of the insulator 71. The insulator 72 holds a contact terminal 73. Lead portions of the electrodes 31, 32, and 33, and the heating element 542 are led out to the proximal end portion of the sensor element 1 and connected to the contact terminal 73. Lead wires 74 connected to the contact terminal 73 are held by a bush 76 inside the cover 75 attached to the proximal end side of the housing 70.

The sensor electrode 32 is made of a Pt—Rh alloy that contains 30 mass % to 70 mass % Pt and 70 mass % to 30 mass % Rh, when an overall noble metal component is 100 mass %. A variation amount of the Rh content in the Pt—Rh alloy from the outermost surface 101 of the sensor electrode 32 to a depth of 350 nm in the thickness direction T of the sensor electrode 32 is within a range of up to 10 mass %. The Rh is included in the Pt to impart the sensor electrode 32 with catalytic activity relative to NOx, which serves as the specific gas component.

The Pt—Rh alloy in the sensor electrode 32, the Pt—Au alloy in the pump electrode 31, and the Pt in the reference electrode 33 are all in particulate form. In addition to the particles of noble metal, the sensor electrode 32, the pump electrode 31, and the reference electrode 33 each contain 10 mass % to 20 mass % solid electrolyte in particulate form, with the entirety of each electrode 31, 32, and 33 being 100 mass %. The solid electrolyte is made of the same component as the solid electrolyte body 2. The solid electrolyte contained in the electrodes 31, 32, and 33 serves to form a three-phase interface of the noble metal component, the solid electrolyte, and the gas to be measured G, when oxygen, NOx, and the like are decomposed. In addition, the solid electrolyte contained in the electrodes 31, 32, and 33 also serves as common material for sintering with the solid electrolyte body 2.

Grooves and gaps for forming the three-phase interface are formed in each electrode 31, 32, and 33. In addition, in each electrode 31, 32, and 33, a state is formed in which the solid electrolyte is mixed with the noble metal component that is in the particulate form, and the noble metal component is mixed with the solid electrolyte that is in the particulate form. Decomposition performance for oxygen, NOx, and the like at the three-phase interface is ensured.

The specific gas component in the gas to be measured G is decomposed at the three-phase interface at which the specific gas component comes into contact with the layer of Pt—Rh alloy in the sensor electrode 32 and the solid electrolyte layer. Then, as a result of the decomposition, oxygen ions migrate to the reference electrode 33 via the solid electrolyte body 2. As a result, the current for measuring the concentration of the specific gas component is detected.

The Pt content and the Rh content of the Pt—Rh alloy in the sensor electrode 32 can be determined by taking into consideration improvement in the catalytic activity of the sensor electrode 32 relative to NOx, which serves as the specific gas component, and prevention of peeling of the sensor electrode 32 due to repeated cooling and heating during use of the gas sensor 100.

When the Rh content of the Pt—Rh alloy in the sensor electrode 32 is less than 30 mass %, a problem arises in that the catalytic activity of the sensor electrode 32 decreases. Meanwhile, when the Rh content of the Pt—Rh alloy in the sensor electrode 32 exceeds 70 mass %, a problem arises in that peeling of the sensor electrode 32 occurs with repeated cooling and heating during use of the gas sensor 100 due to the effects of Rh that is more prone to thermal expansion than Pt.

The particle size of the Pt—Rh alloy is within a range of 0.5 µm to 5 µm. Here, the particle size of the Pt—Rh alloy is determined based on the length of the longest straight line among straight lines drawn through a particle, regardless of the shape of the particle. The particles of the Pt—Rh alloy are connected to each other by sintering. However, the particle size can be measured through observation under a light microscope or an electron microscope. For example, the particle size can be measured by a cross-section of the sensor electrode 32 or the like being exposed by ion beam processing or the like, and the cross-section being observed under a scanning electron microscope (SEM) or the like.

When the particle size of the Pt—Rh alloy is less than 0.5 µm, sintering caused by heat from the particles advances during use of the gas sensor 100, and aggregation tends to occur in the sensor electrode 32. Meanwhile, when the particle size of the Pt—Rh alloy exceeds 5 µm, the specific surface area of the sensor electrode 32 becomes small. In both cases, the catalytic activity of the sensor electrode 32 relative to the specific gas component may decrease.

The Rh in the Pt—Rh alloy of the sensor electrode 32 is in the form of a metal that contains very little oxides. The thickness of the sensor electrode 32 is within a range of 5 µm to 20 µm.

Figure 3:
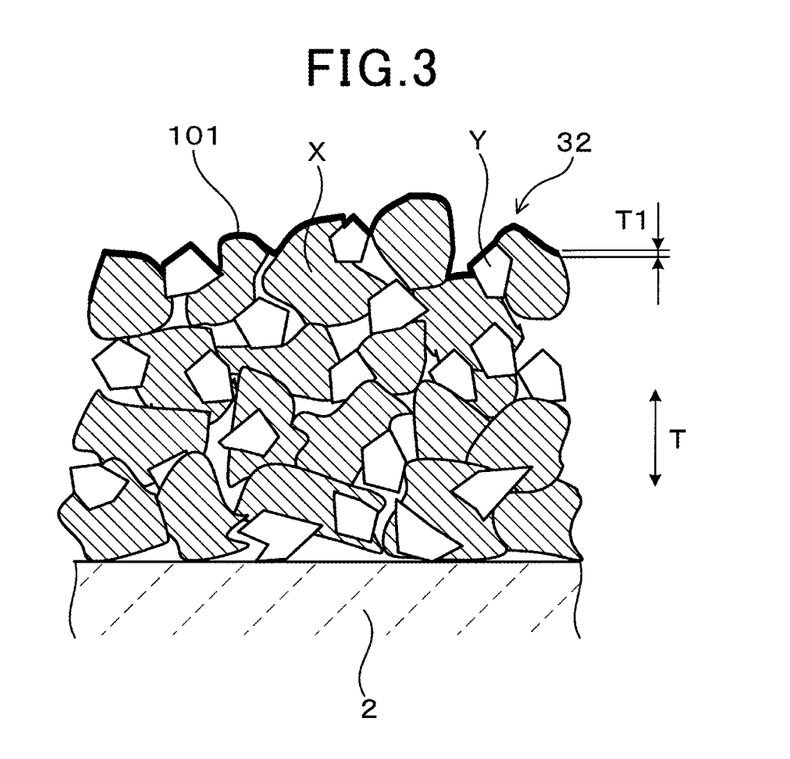
FIG. 3 is an explanatory diagram schematically showing an enlarged view of a portion of a sensor electrode according to the embodiment.

FIG. 3 schematically shows a surface region T1 from the outermost surface 101 of the sensor electrode 32 to a depth of 350 nm. As shown in FIG. 3, the outermost surface 101 of the sensor electrode 32 has a complex, uneven shape formed by numerous particles X of the Pt—Rh alloy and numerous particles Y of the solid electrolyte. Numerous pores that are recessed in a groove-like manner are formed on the surface of the outermost surface 101. The surface region T1 from the outermost surface 101 of the sensor electrode 32 to a depth of 350 nm refers to an area measured from each surface composing the uneven shape, in the thickness direction T of the sensor electrode 32 and the sensor element 1, along the uneven shape. The surface region T1 can be considered to be a surface layer of the sensor electrode 32 along the uneven shape. The surface region T1 can be considered to be a surface layer of the particles of the Pt—Rh alloy that range in size from 0.5 µm to 5 µm, from the outermost surface 101 to a depth of 350 nm in the thickness direction T.

Segregation in the thickness direction (depth direction) T and a planar direction is hardly present in the Rh in the Pt—Rh alloy contained in the overall sensor electrode 32. Here, a state in which segregation is hardly present can be considered to be a state in which the variation amount of the Rh content in the Pt—Rh alloy is within the range of up to 10 mass %. When the variation amount exceeds the range of up to 10 mass %, segregation can be considered present.

The Pt—Rh alloy in the sensor electrode 32 according to the present embodiment contains 60 mass % Pt, and 40 mass % Rh. The Pt content and the Rh content are expressed as average values for the overall sensor electrode 32. In addition, a state in which the variation amount of the Rh content of the Pt—Rh alloy in the surface region T1, from the outermost surface 101 of the sensor electrode 32 to a depth of 350 nm in the thickness direction T, is within a range of up to 10 mass % indicates that the difference between the maximum Rh content and the minimum Rh content in the surface region T1 is within 10 mass %. In addition, the variation amount of the Rh content of the Pt—Rh alloy in the surface region T1, from the outermost surface 101 of the sensor electrode 32 to a depth of 350 nm in the thickness direction T, according to the present embodiment is within a range of up to 5 mass %.

Here, the numeric value, "depth of 350 nm," is prescribed based on the fact that, upon experimental measurement of the depths at which Rh segregation may be present, the measurement results indicate that segregation is not found in positions located deeper than the depth of 350 nm.

An allowable variation amount of the Rh content of the Pt—Rh alloy is determined in the following manner.

The allowable variation amount is determined under a condition that, when thermal endurance time R is 5400 (Hr), an output change amount of the gas sensor 100 falls within a range of ±10 mass % during the thermal endurance time R. The thermal endurance time R is a target amount of time for long-term use of the gas sensor 100. The output change amount serves to express a change amount of the sensitivity of the sensor electrode 32 to the specific gas component.

Figure 4:
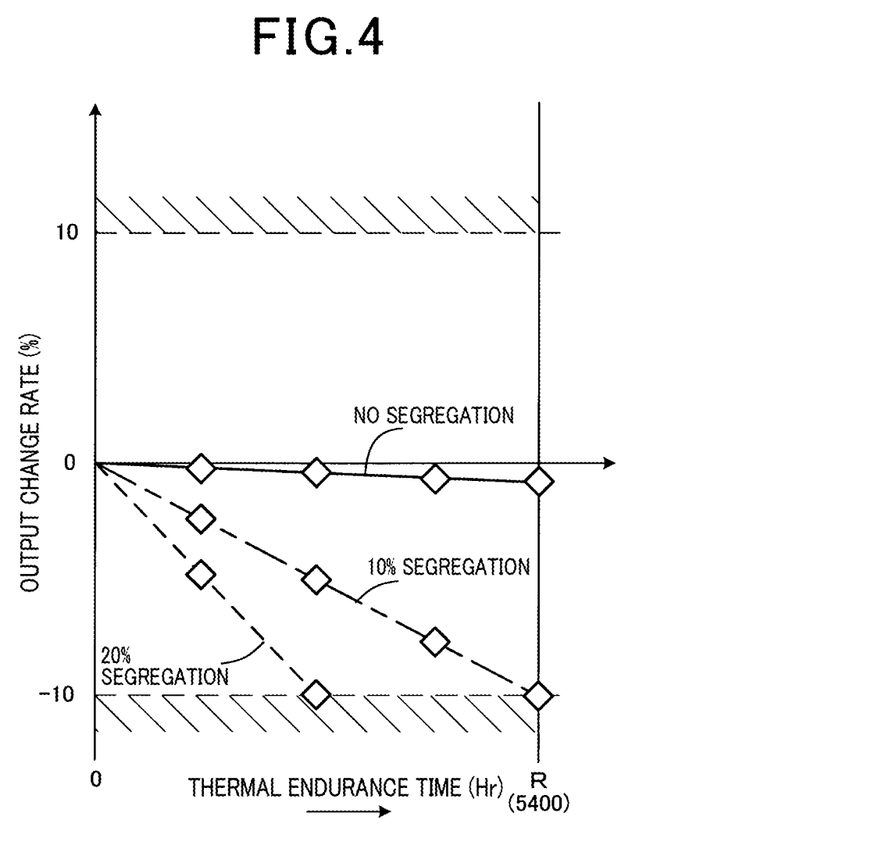
FIG. 4 is a graph of a relationship between thermal endurance time and output change amount of the gas sensor according to the embodiment.

FIG. 4 shows a relationship between the thermal endurance time (Hr) and the output change amount (%) of the gas sensor 100. The output change amount indicates the amount of change in the output of the gas sensor 100 with time, when the output at an initial state of the gas sensor 100 is 0%, which serves as reference.

FIG. 4 shows the results of measurement of the output change amount of the gas sensor 100 when segregation in the Rh content of the Pt—Rh alloy is hardly present, when segregation of 10% is present, and when segregation of 20% is present, within the surface region T1.

When, segregation (variation) in the Rh content of the Pt—Rh alloy is hardly present within the surface region T1, it is clear that the output change amount of the gas sensor 100 after an elapse of 5400 (Hr) is minimal.

In addition, when segregation (variation) in the Rh content of the Pt—Rh alloy within the surface region T1 is 10 mass %, the output change amount of the gas sensor 100 after the elapse of 5400 (Hr) falls within the range of up to −10 mass %. Furthermore, when segregation (variation) in the Rh content of the Pt—Rh alloy within the surface region T1 is 20 mass %, the output change amount of the gas sensor 100 after the elapse of 5400 (Hr) exceeds the range of up to −10 mass %.

Based on these results, it is confirmed that the allowable variation amount of the Rh content of the Pt—Rh alloy is 10 mass %. It is also found that, as a result of the Rh content of the Pt—Rh alloy being within the range of up to 10 mass %, the output change amount of the gas sensor 100 can be kept within the allowable range.

The sensor electrode 32 is formed by the plate-shaped solid electrolyte body 2 being coated with an electrode paste. The solid electrolyte body 2 and the electrode paste are then sintered. The electrode paste contains the Pt—Rh alloy, the solid electrolyte, a solvent, and the like. When sintering is performed, a portion of the Rh in the Pt—Rh alloy reacts with oxygen and produces $Rh_2O_3$. Then, after sintering, an energization process is performed between the sensor electrode 32 and the reference electrode 33. The $Rh_2O_3$ formed on the surface of the sensor electrode 32 is thereby reduced. At this time, segregation of Rh near the surface of the sensor electrode 32 is lessened. However, the segregation of Rh lessened by the energization process is only segregation located near the surface of the sensor electrode 32.

Rh readily reacts with oxygen. It is thought that, in an environment in which oxygen is present in the periphery of the sensor electrode 32, the Rh in the Pt—Rh alloy of the sensor electrode 32 gathers near the surfaces of the particles X of the Pt—Rh alloy and near the surface of the sensor electrode 32, such as to be drawn to the oxygen.

Figure 5:
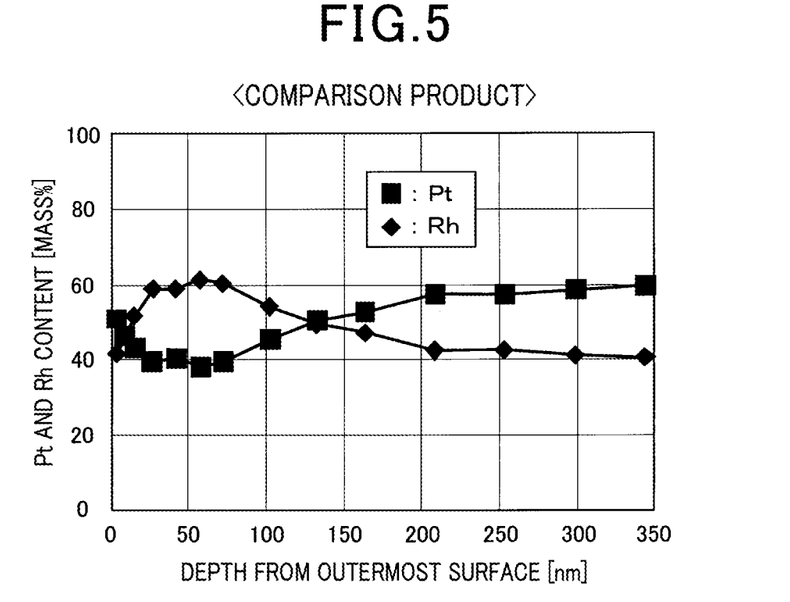
FIG. 5 is a graph of a relationship between depth (nm) in a thickness direction from an outermost surface of a sensor electrode, and Pt and Rh contents (mass %) of a Pt—Rh alloy in the sensor electrode of a comparative product according to the embodiment.
Figure 6:
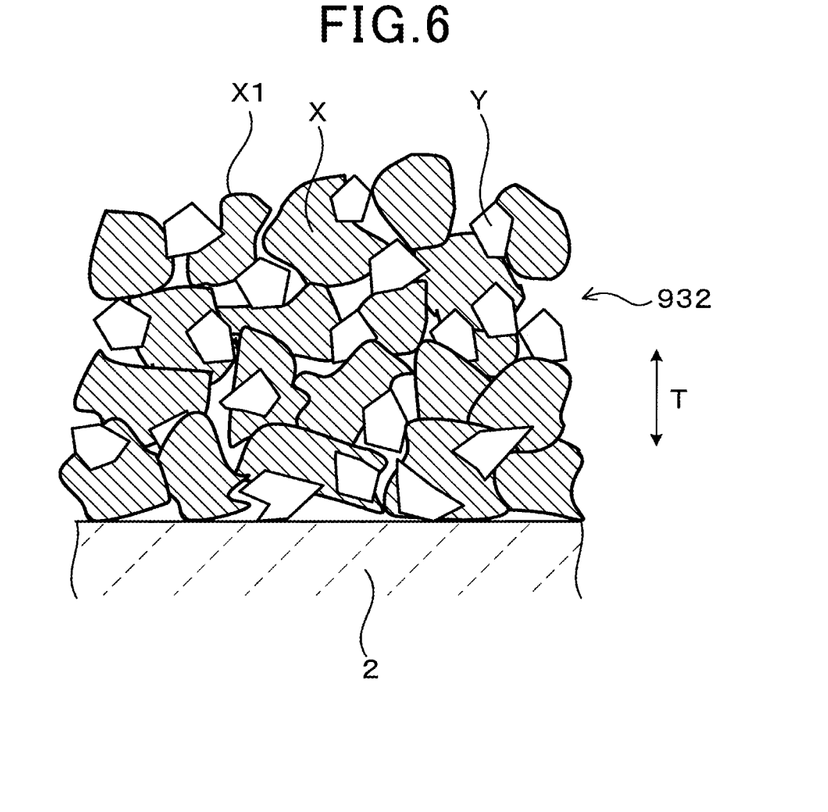
FIG. 6 is an explanatory diagram schematically showing an enlarged view of a portion of the sensor electrode of the comparative product according to the embodiment.

FIG. 5 shows the results of an analysis of the distribution of Pt and Rh in the Pt—Rh alloy in the surface region T1, from the outermost surface 101 to a depth of 350 nm in the thickness T direction, in a conventional sensor electrode 932 (comparative product) (see FIG. 6). The analysis was performed on the particles of the Pt—Rh alloy in the sensor element 932 using X-ray photoelectron spectroscopy (XPS). More specifically, the analysis was performed while cutting away an area having an analysis area diameter of Φ400 μm, in an electrode depth direction at a speed of 0.01 nm/sec, using ESCALAB 200 manufactured by VG Scientific (UK)

In FIG. 5, segregation of Rh is present in the vicinity of a depth of 25 nm to 100 nm in the thickness direction T, from the outermost surface 101 of the sensor electrode 932. The Rh content of the Pt—Rh alloy is high. The Rh content in the vicinity of a depth of 25 nm to 75 nm is about 20 mass % higher than the 40 mass % that is the average Rh content. The segregation of Rh in the conventional sensor electrode 932 is that which could not be reduced by the energization process performed between the sensor electrode 932 and the reference electrode 33.

FIG. 6 schematically shows the state of the conventional sensor electrode 932 (comparative product) on which the analysis was performed. In FIG. 6, $Rh_2O_3$ (indicated by reference number X1) that forms the segregation of Rh in the Pt—Rh alloy is present near the surfaces of the particles X of the Pt—Rh alloy. The Rh content itself of the Pt—Rh alloy in the overall sensor electrode 932 does not change. However, in the surface region T1 from the outermost surface 101 of the sensor electrode 932 to a depth of 350 nm in the thickness direction T, a portion (segregation of Rh) containing a large amount of the Rh in the Pt—Rh alloy is present.

Here, $Rh_2O_3$ is detected only in the results of an analysis performed on the outermost surfaces of the particles X of the Pt—Rh alloy. The depth to which $Rh_2O_3$ is formed is unclear.

Figure 7:
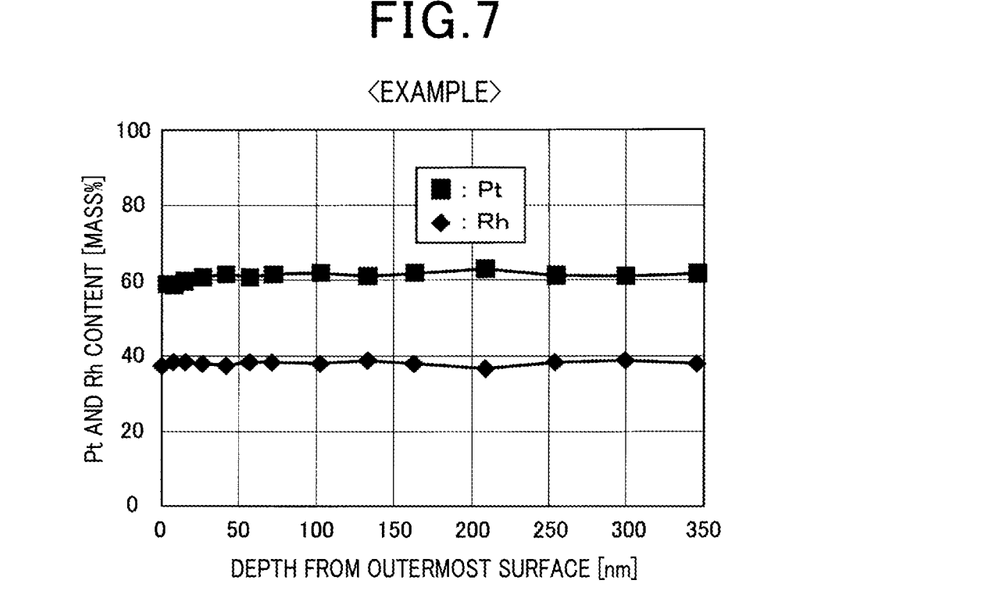
FIG. 7 is a graph of a relationship between depth (nm) in a thickness direction from an outermost surface of the sensor electrode, and Pt and Rh contents (mass %) of a Pt—Rh alloy in the sensor electrode of an example product according to the embodiment.

Meanwhile, FIG. 7 shows the results of an analysis of the distribution of Pt and Rh in the Pt—Rh alloy in the surface region T1, from the outermost surface 101 to a depth of 350 nm in the thickness T direction, in the sensor electrode 32 according to the present embodiment. The analysis was performed by a method similar to that for the conventional sensor electrode 32.

In FIG. 7, segregation of Rh is hardly present in the surface region T1, from the outermost surface 101 of the sensor electrode 32 to a depth of 350 nm in the thickness T direction. A variation range of the Rh content of the Pt—Rh alloy is about 3 mass %.

Figure 8:
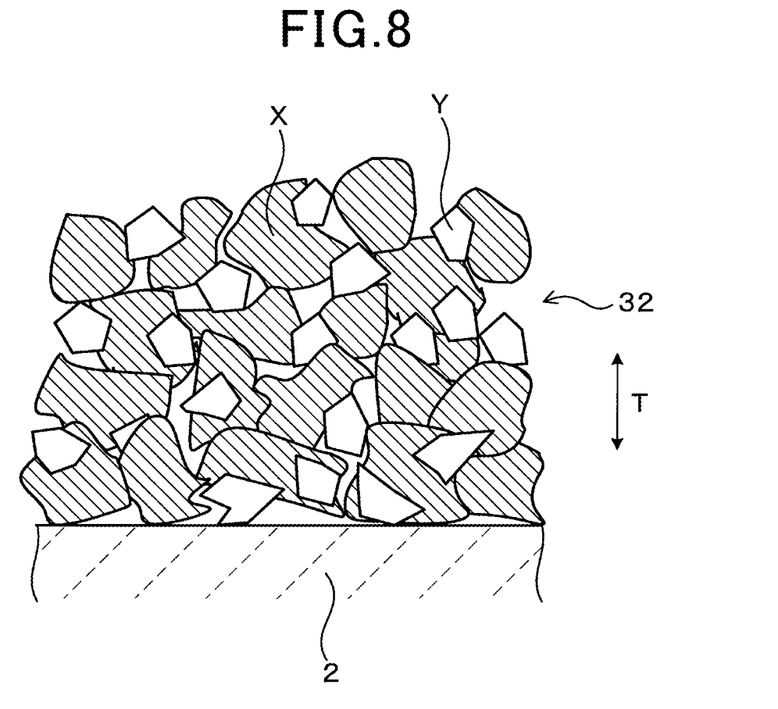
FIG. 8 is an explanatory diagram schematically showing an enlarged view of a portion of the sensor electrode of the example product according to the embodiment.

FIG. 8 schematically shows the state of the sensor electrode 32 (example product) according to the present embodiment on which the analysis was performed. In FIG. 8, $Rh_2O_3$ is hardly present near the surfaces of the particles X of the Pt—Rh alloy. In addition, segregation of Rh in the Pt—Rh alloy is hardly present in the surface region T1, from the outermost surface 101 of the sensor electrode 32 to a depth of 350 nm in the thickness T direction.

The sensor element 1 according to the present embodiment is formed by a sintering process being performed on a laminate body in which the plate-shaped solid electrolyte body 2, the electrodes 31 to 33, the insulators 51 to 53, and the heater 54 are integrated. The sintering process is performed in a nitrogen atmosphere. In the sintering process, oxygen in the nitrogen atmosphere cannot be completely eliminated. The Rh near the surface of the sensor electrode 32 is oxidized, and $Rh_2O_3$ is formed near the surface.

In addition, the sensor element 1 placed in the nitrogen atmosphere, and the energization process is performed between the sensor electrode 32 and the reference electrode 33. At this time, in the sensor electrode 32, the Pt—Rh alloy is dispersed among the solid electrolyte, and pores through which the gas to be measured G flows are formed. In addition, in the reference electrode 33, the Pt is dispersed among the solid electrolyte, and pores through which the reference gas A flows are formed.

When the energization process is performed, a portion of the $Rh_2O_3$ formed near the surface of the sensor electrode 32 is reduced. However, a phenomenon in which oxygen escapes from the solid electrolyte body 2 also occurs. Therefore, to replenish the solid electrolyte body 2 with oxygen, a reoxidation process is performed. When the reoxidation process is performed, the measured gas chamber 41 has a reducing air atmosphere that is 0.2 volume % to 1 volume % hydrogen that serves as the reducing gas. The remaining portion is nitrogen. The reducing gas atmosphere can also contain carbon monoxide, hydrocarbon, or the like, instead of hydrogen. In addition, the reference gas chamber 42 has an atmospheric air atmosphere.

The sensor element 1 is then heated to an appropriate temperature at which the solid electrolyte body 2 has oxygen ion conductivity. The sensor element 1 is left to stand for a predetermined amount of time. At this time, due to the difference in oxygen concentration between the atmospheric air atmosphere and the reducing gas atmosphere, oxygen ions are conducted from the reference gas chamber 42 to the measured gas chamber 41 via the solid electrolyte body 2. As a result, the solid electrolyte body 2 is replenished with oxygen. The sensor element 1 according to the present embodiment in which the sensor electrode 32 has little segregation of Rh can be formed by modifications, that is, an environment in which oxygen molecules are not present near the surface of the sensor electrode 32 being formed, and oxygen ions being conducted to the sensor electrode 32 in the measured gas chamber 41 from the reference electrode 33 in the reference gas chamber 42, during the reoxidation process.

In addition, as a result of the reference gas chamber 42 being formed in the sensor element 1, sufficient oxygen can be supplied to the reference electrode 33 during the reoxidation process, and conduction of oxygen ions from the reference electrode 33 to the sensor electrode 32 can be facilitated. Therefore, when the sensor element 1 in which the sensor electrode 2 has little segregation of Rh is manufactured, it is important that the reference gas chamber 42 is formed in the sensor element 1.

In the sensor element 1 according to the present embodiment, even when segregation of Rh is present within the surface region T1 from the outermost surface 101 of the sensor electrode 32 to a depth of 350 nm in the thickness direction T, the segregation falls within the range of the variation amount of up to 10 mass %. A state in which Rh that exhibits catalytic activity relative to NOx is segregated near the surface of the sensor electrode 32 is resolved. Therefore, when the sensor element 1 is heated and the gas sensor 100 is in use, changes in the distribution of Pt and Rh in the Pt—Rh alloy of the sensor electrode 32 hardly occur. Consequently, during use of the gas sensor 100, the sensitivity of the sensor electrode 32 to NOx does not easily vary.

Thus, in the gas sensor 100 according to the present embodiment, the occurrence of variations with time in the detection accuracy for NOx can be suppressed.

The present disclosure is not limited only to the embodiment. Other embodiments are also possible without departing from the spirit of the invention.

What is claimed is:

1. A gas sensor comprising:
a sensor element that detects gas concentration,
the sensor element comprising:
a solid electrolyte body that has oxygen ion conductivity, the solid electrolyte body including a first main surface that is exposed to a gas to be measured and a second main surface that is exposed to a reference gas;
a sensor electrode that is provided on the first main surface of the solid electrolyte body, and detects a specific gas component in the gas to be measured; and
a reference electrode that is provided on the second main surface of the solid electrolyte body,
the sensor electrode being made of a Pt—Rh alloy that contains 30 mass % to 70 mass % Pt and 70 mass % to 30 mass % Rh, when an overall noble metal component is 100 mass %,
a variation amount of the Rh content of the Pt—Rh alloy from an outermost surface of the sensor electrode to a depth of 350 nm in a thickness direction of the sensor electrode being within a range of up to 10 mass %.

2. The gas sensor according to claim 1, wherein:
particles configuring the Pt—Rh alloy are within a range of 0.5 μm to 5 μm in size.

3. The gas sensor according to claim 1, wherein:
the sensor element further comprises:
a measured gas chamber into which the gas to be measured is introduced, the measured gas chamber being provided on the first main surface of the solid electrolyte body;
a reference gas chamber into which the reference gas is introduced, the reference gas chamber being provided on the second main surface of the solid electrolyte body; and
a pump electrode for adjusting oxygen concentration of the gas to be measured in the measured gas chamber, the pump electrode being provided in the solid electrolyte body in a position further towards an upstream side of a flow of the gas to be measured than a position in which the sensor electrode is provided.

4. The gas sensor according to claim 2, wherein:
the sensor element further comprises:
a measured gas chamber into which the gas to be measured is introduced, the measured gas chamber being provided on the first main surface of the solid electrolyte body;

a reference gas chamber into which the reference gas is introduced, the reference gas chamber being provided on the second main surface of the solid electrolyte body; and a pump electrode for adjusting oxygen concentration of the gas to be measured in the measured gas chamber, the pump electrode being provided in the solid electrolyte body in a position further towards an upstream side of a flow of the gas to be measured than a position in which the sensor electrode is provided.

* * * * *